(12) United States Patent
Zhang

(10) Patent No.: US 6,476,233 B1
(45) Date of Patent: Nov. 5, 2002

(54) TRANSITION METAL-CATALYZED REACTIONS BASED ON CHIRAL AMINE OXAZOLINYL LIGANDS AND RELATED COMPOUNDS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/712,139

(22) Filed: Nov. 15, 2000

Related U.S. Application Data

(63) Continuation-in-part of application No. 09/189,867, filed on Nov. 12, 1998.
(60) Provisional application No. 60/165,483, filed on Nov. 15, 1999.

(51) Int. Cl.$^7$ .......................... C07D 263/28; B01J 31/02
(52) U.S. Cl. ..................... 548/238; 548/237; 548/312.4; 548/146; 502/152
(58) Field of Search ................................ 548/237, 238, 548/312.4, 146; 502/152

(56) References Cited

U.S. PATENT DOCUMENTS

| | | |
|---|---|---|
| 3,192,224 A | 6/1965 | Kapar |
| 3,872,096 A | 3/1975 | Witte et al. |
| 3,979,405 A | 9/1976 | Toth et al. |
| 4,497,812 A | 2/1985 | Creuzet et al. |

OTHER PUBLICATIONS

Noyori, R. & Hashiguchi, S., "Asy mmetric Transfer Hydrogenation Catalyzed by Cataly zed by Chiral Ruthenium Complexes," *Acc. Chem. Res.,* 30, 97–102 (1997).
Haack, K.–J. et al., "The Cataly st Precursor, Cataly st, and Intermediated in the $R_u$–Prom oted Asymmetric–Hydrogen Transfer between Alcohols and Ketones," *Angew . Chem. Int. Ed. Eng.,*36 No. 3 (1997).
Gamez, P. et al., "Asymmetric Catalytic Reduction of Carbonyl Compounds Using $C_2$ Sy mmetric Diamines as Chiral Ligands," *Tetrahedron: Asym metry,*vol. 6, No. 3, 705–718 (1995).
Nishiyama, H. et al., "New Chiral Ruthenium Bis(oxazolinyl)pyridine Catalyst. Effiecient Assymmetrict Cyclopropanation of Olefins with Diaz oacetates," *J. Am. Chem. Soc.,* 116, 2223–2224 (1994).
Dox, A.W., "Acetamidine Hydrochloride," *Organic Syntheses,* vol. 1, 5–7 (1932).
Zassinovich, G. et al., "Asymmetric Hydrogen Transfer Reactions Promoted by Homogeneous Transition Metal Cataly sts," *Chem. Rev.,* 92, 1051–1069 (1992).
Nishiyama, H. et al., "Chiral Ruthenium (II)–Bis–(2–oxazolin–2–yl)pyridine Com plexes. Asymmeteric Catlaytic Cyclopropanation of Olefins and Diazoacetates," *Bull. Chem. Soc. Jpn.,* 68, 1247–1262 (19950.

Evans, D. et al., "$C_2$–Sy mmetric Cationic Copper(II) Com plexes as Chiral Lewis Acids: Counterion Effects in the Enantioselecti e Diels–Alder Reaction," *Angew. Chem. Int. Ed. Engl.,* 34, No. 7 (1995).
Evans, D. et al., "$C_2$–Sy mmetric Cationic Copper(II) Com plexes as Chiral Lewis Acids. Cataly tic Enantioselective Aldol Additions of Silylketene Acetals to (Benzyloxy)acetaidehyde," *J. Am. Chem. Soc.,* 118, 5814–5815 (1996).
de Graauw, C.F. et al., "Meerwein–Pondorf–Verley Reductions and O ppenauer Oxidations: An Integrated Approach," *Journal of Synthetic O rganic Chemistry,* No. 10, 1007–1010 (1994).
Jiang, Y. et al., "Highly Effective NPN–type Tridentate Ligands for Asymmetric Transfer Hydrogenation of Ketones," *Tetrahedron Letters,* vol. 38, No. 2, 215–218 (1997).
Jiang, Q. et al., "Synthesis of (1R, 1R )–2,6–Bis[1–(dipheny lphoshino)ethy l]pyridine and its Application in Asy mmetric Transer Hydrogenation," *Tetrahedron Letters,* vol. 37, No. 6, 797–800 (1996).
Sammakia, T. & Strangeland, E., "Transfer Hydrogenation with Ruthenium Complexes of Chiral (Phosphinoferrocenyl)oxazonlines," *J. Org. Chem.,* 62, 6104–6105 (1997).
Evans, D. et al., "A Chiral Sam arium–Based Cataly st for the Asymmetric Meerwein–Ponndorf–Vertley Reduction," *J. Am. Chem. Soc.,* 115, 9800–9801 (1993).
Muller, D. et al., "21.$C_2$–Sy mmetric 4,4',5,5'–Tetrahydrobi)oxazoles) and 4,4',5,5'–Tetrahydro–2,2'–methylenebis [oxazoles] as Chiral Ligands f or Enantioselectiv e Catalysis," *Helvetica Chim ica Acta,* vol. 74, 232–239 (1991).
Langer, T. & Helmchen, G., "Highly Efficient New Cataly sts for Enantioselective Transfer Hydrogenation of Ketones," *Tetrahedron Letters,* vol. 37, No. 9, 1381–1384 (1996).
Gao, J–X et al., "A Ruthenium (II) Complex with a $C_2$–Symmetric Diphosphine/Diam ine Tetradentate Ligand for Asymmetric Transfer Hydrogenation of Aromatic Ketones," *Organometallics,* 15, 1087–1089 (1996).
Nishiyama, H., et al., Chiral and $C_2$–Sy mmetric Bis(oxazolinylpyridine)rhodium (III) Compleses: Effective Catalysts for Asymmetric Hydrosilylation of Ketones, *Organometallics,* 8, 846–848 (1989).

(List continued on next page.)

Primary Examiner—Floyd D. Higel
Assistant Examiner—Kamal Saeed
(74) Attorney, Agent, or Firm—Finnegan, Henderson, Farabow, Garrett & Dunner, L.L.P.

(57) ABSTRACT

This invention is to develop novel transition metal catalysts for the practical synthesis of important chiral molecules. The invention emphasizes asymmetric catalysis based on chiral amine oxazolinyl ligands and related ligands. Specially, a direct asymmetric hydrogenation system based on Ru-Ambox catalyst was discovered.

13 Claims, 9 Drawing Sheets

OTHER PUBLICATIONS

Jiang, Y. et al., "New Chiral Ligands f or Catlytic Asymmetric Transfer Hydrogenation of Ketones," *Tetrahedron Letters*, vol. 38, No. 37, 6565–6568 (1997).

Nishiyamam, H., et al., Highly Enantioselective Hydrosilylation of Ketones with Chiral and $C_2$–Symmetrical Bis(oxazolinyl)pyridine–Rhodium Catalysts, *Organometallics*, 10, 500–508 (1991).

Corey, E.J., et al., "Designed Catalyst for Enantioselective Diels–Alder Addition from a $C_2$–Symmetric Chiral Bis(oxazoline)–Fe(III) Complex," *J. Am. Chem. Soc.*, 113, pp. 728–729 (1991).

Jiang, Yutong, et al., "A New Chiral Bis(oxaz olinylmethyl)amine Ligand for Ru–Cataliz ed from a Assymmetric Transfer Hydrogenation of Ketones," *J. Am. Chem. Soc.*, 120, pp. 3817–3818 (1998).Ghosh, Arun K., et la., "$C_2$–Symmetric Chiral Bis(oxazolin)–Metal Complexes in Catalytic Asymmetric Synthesis," Tetrahedron: Asymmetry vol. 9, pp. 1–45 (1998).

Ghosh, Arun K., et al., "$C_2$–Sym metric Chiral Bis(oxaz oline)–Metal Complexes in Catalytic Asymmetric Synthesis," Tetrahedron: Asy mmetry vol. 9, pp. 1–45 (1998).

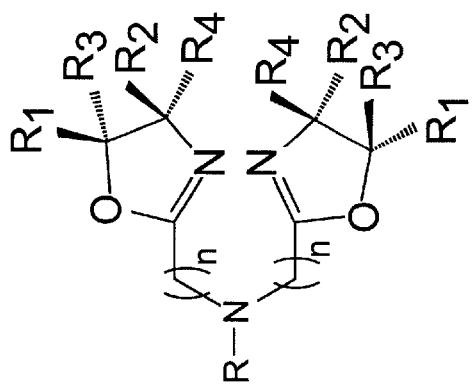

FIG. 1

R, R1, R2, R3, R4 = H, alkyl, aryl, substituted alkyl, substituted aryl. Ring structure is also possible by linking any two R groups from R1 to R4. The ligands can be linked to solid supports.

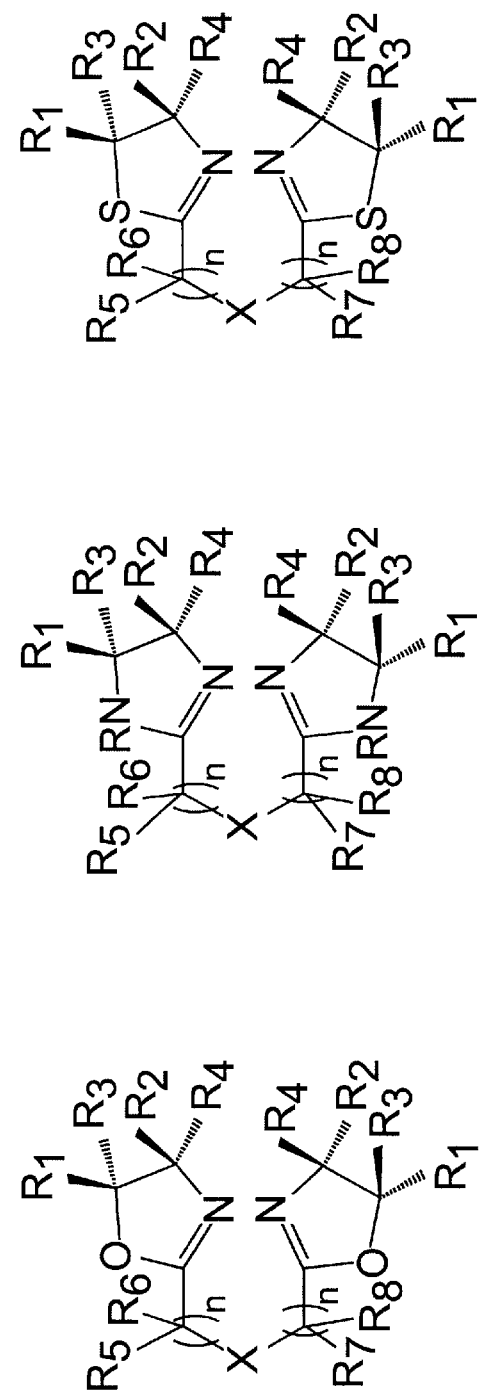

FIG. 2

R, R1, R2, R3, R4, R5, R6, R7, R8 = H, alkyl, aryl, substituted alkyl, substituted aryl. Ring structure is also possible by linking any two R groups from R1 to R4. The ring can be alkyl, substituted alkyl, aryl, and substituted alryl. X = PR', PH, O, S, Se, AsR', AsH, SiR'H, GeR'H, NH, NR', NR'$_2$, NCOR', NOH, NNHR', NNHCOR' wherein R' = alkyl, aryl, substituted alkyl, and substituted aryl. n = 1, 2.

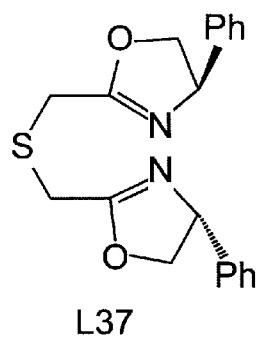 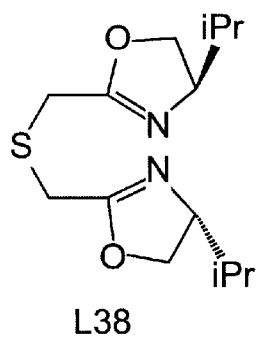 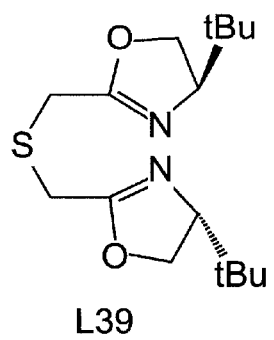
L37        L38        L39
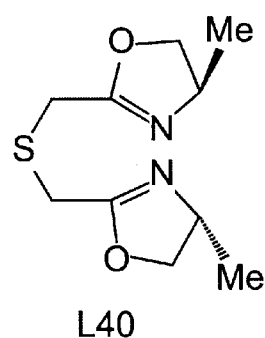 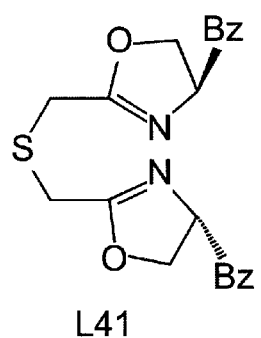 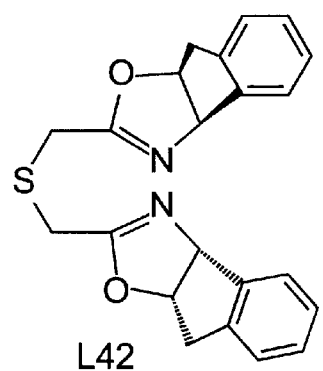
L40        L41        L42
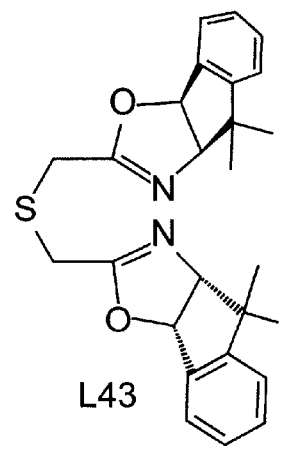 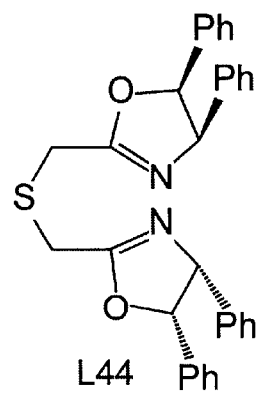 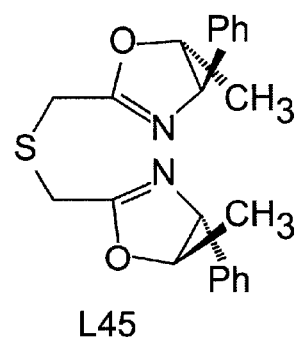
L43        L44        L45
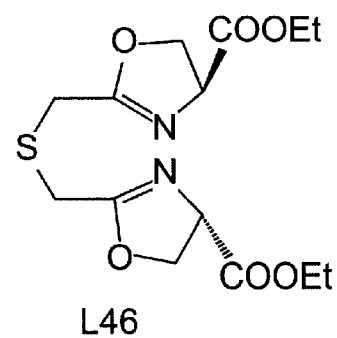 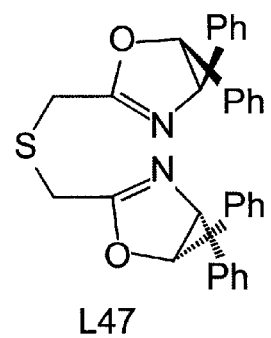 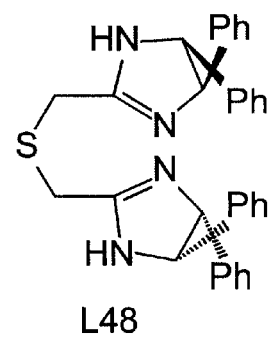
L46        L47        L48
*FIG. 6*

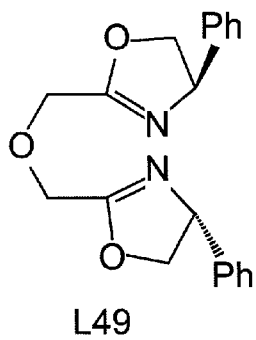
L49
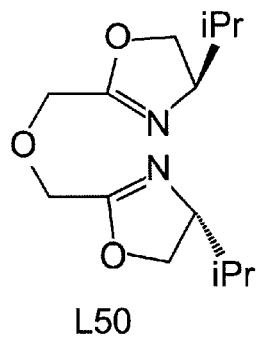
L50
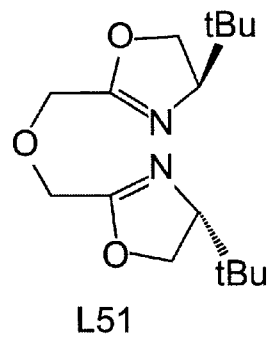
L51
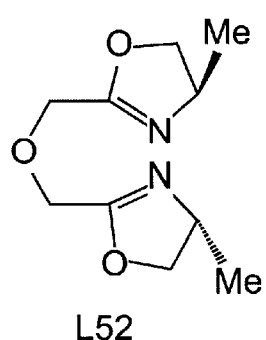
L52
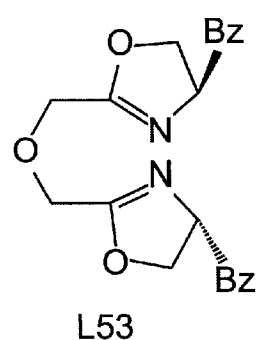
L53
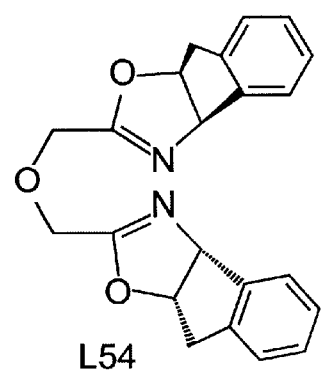
L54
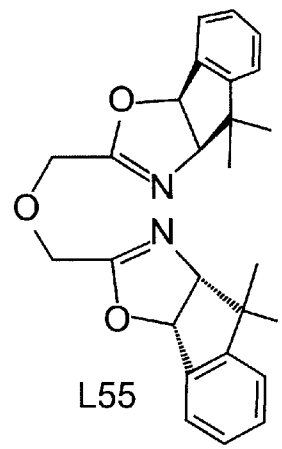
L55
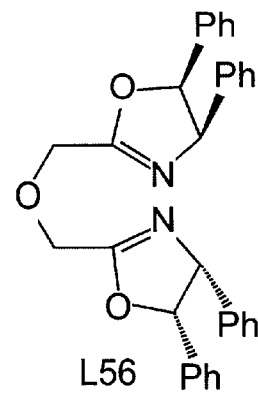
L56
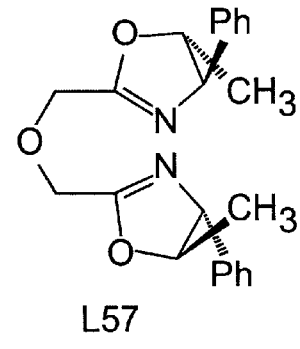
L57
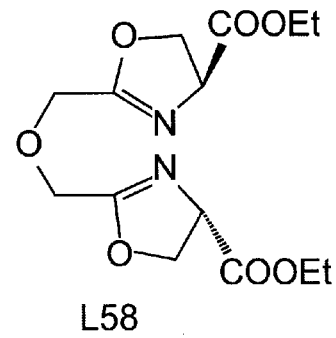
L58
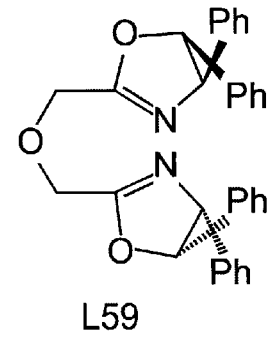
L59
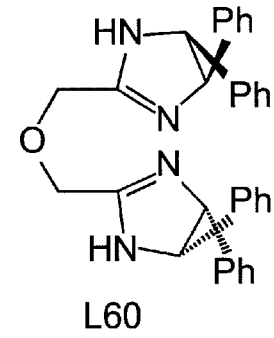
L60
*FIG. 7*

Schematic depiction of transition metal catalysts of chiral tridentate nitrogen ligands with an NH function. Cycli (transition state of transfer hydrogenation of prochiral ketones.

TRANSITION METAL-CATALYZED REACTIONS BASED ON CHIRAL AMINE OXAZOLINYL LIGANDS AND RELATED COMPOUNDS

This is a continuation-in-part of Application Ser. No. 09/189,867, filed Nov. 12, 1998, and claims the benefit of U.S. Provisional Application No. 60/165,483, filed Nov. 15, 1999, all of which are incorporated herein by reference in its entirety. Government funding was provided by the National Institute of Health under NIH Fund No. RO1 GM 58832-01A1.

SUMMARY OF THE INVENTION

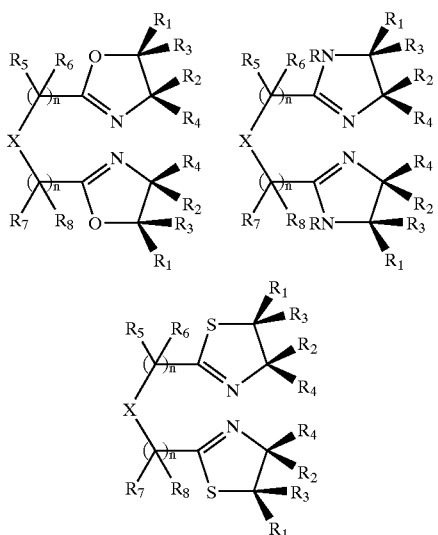

R, R1, R2, R3, R4, R5, R6, R7, R8 = H, alkyl, aryl, substituted alkyl, substituted aryl. Ring structure is also, possible by linking any two R groups from R1 to R4. The ring can be alkyl, substituted alkyl, aryl, and substituted aryl. X = PR', PH, O, S, Se, AsR', AsH, SiR'H, GeR'H, NH, NR', NR'2, NCOR', NOH, NNHR', NNHCOR' wherein R' = alkyl, aryl, substituted alkyl, and substituted aryl. n = 1, 2.

This invention covers several new families of chiral amine oxazolinyl ligands and related ligands for asymmetric catalysis. There are many examples of oxazolinyl ligands linked with O, N, P, S, Se, in the of the groups. Oxazolinyl groups can be easily made from chiral amino alcohols. These ligands can be used for many asymmetric catalytic reactions. For examples, chiral tridentate ligands are highly effective for Ru-catalyzed transfer hydrogenation and direct hydrogenation of ketones and imines. Many other transition metal-catalyzed reactions such as hydrogenation, hydride transfer reaction, hydrosilylation, hydroboration, hydrovinylation, hydroformylation, hydrocarboxylation, arrangement, allylic alkylation, cyclopropration, Diels-Alder reaction, Aldol reaction, Heck reaction and Michael addition are also possible.

The invention covers ligands as well as procedures for asymmetric catalytic reactions. FIG. 2 describes the general structure of this ligand. In these ligands, R, R1, R2, R3, R4, R5, R6, R7, R8=H, alkyl, aryl, substituted alkyl, substituted aryl. Ring structure is also possible by linking any two R groups from R1 to R4. The ring can be alkyl, substituted alkyl, aryl, and substituted aryl. X=PR', PH, O, S, Se, AsR', AsH, SiR'H, GeR'H, NH, NR', NR'2, NCOR', NOH, NNHR', NNHCOR' wherein R'=alkyl, aryl, substituted alkyl, and substituted aryl, n=1, 2.

BACKGROUND OF THE INVENTION

Molecular chirality plays an important role in science and technology. The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects. A growing demand in pharmaceutical industries is to market a chiral drug in enantiomerically pure form. To meet this fascinating challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule. During the last two decades, great attention has been devoted to discovering new asymmetric catalysts and more than a half-dozen commercial industrial processes have used asymmetric catalysis as the key step in the production of enantiomerically pure compounds. The worldwide sales of chiral drugs in 1994 is 45.3 billion dollars, which enjoy 27% increase from the sales in 1993 (35.6 billions).

Many chiral phosphines have been made to facilitate asymmetric reactions. Among these ligands, BINAP is one of the most frequently used bidentate chiral phosphines. The axially dissymmetric, fully aromatic BINAP ligand has been demonstrated to be highly effective for many asymmetric reactions. Duphos and related ligands have also shown impressive enantioselectivities in numerous reactions. However, these phosphines are difficult to make and some of them are air sensitive. Recently, chiral nitrogen ligands have been extensively studied for asymmetric reactions. Particularly, oxazolinyls derived from chiral amino alcohols are popular ligands. Recognition of secondary interaction between ligands and substrates are also used to design asymmetric catalysts. For example, primary and secondary NH may form H-bond with substrates. Part of this invention is the development of transition metal complexes with families of amine oxazolinyl ligands for practical asymmetric synthesis. A Ru-ambox complex can be used as an effective catalyst for asymmetric transfer hydrogenation of ketones. The current invention emphasizes the chemistry of Ru-catalyzed direct hydrogenation of ketones, a more practical method for making chiral alcohols. In addition, many other ligands are also disclosed.

A variety of asymmetric reactions such as hydrogenation, hydride transfer reaction, hydrosilylation, hydroboration, hydrovinylation, hydroformylation, hydrocarboxylation, allylic alkylation, cyclopropanation, Diels-Alder reaction, Aldol reaction, Heck reaction and Michael addition will be explored based on these innovative ligand systems. The success of this approach would lead to efficient and practical methods for producing important chiral drugs and agrochernicals.

BRIEF DESCRIPTION OF THE FIGURES

FIG. 1 discloses a variety of chiral ligands.

FIG. 2 covers a variety of ligands

FIG. 7 shows examples of ligands (L49 to L60)

DETAILED DESCRIPTION

Asymmetric catalytic transfer hydrogenation using 2-propanol as a hydrogen source offers an attractive route of reducing unsymmetric ketones to chiral alcohols.[1] Among the recently developed efficient transition-metal-based chiral catalysts,[2] the most notably is the Ru(II-TsDPEN (N-(p-tolylsulfonyl)-1,2-diphenylethylene-diamine) system reported by Noyori.[3] They suggest that an NH moiety in the ligand may promote a cyclic transition state through hydrogen bonding to ketone substrate, hence greatly increases substrate affinity to the catalyst active site, inducing high activity and optical purity. Earlier results from Noyori and Lemaire have also shown similar "NH effect".[4,5] In a continuous effort of developing chiral tridentate ligands for asymmetric catalysis,[2a-c] we have designed bis(oxazolinylmethyl)amine (ambox) ligand system. Chiral tridentate ligands tend to form a deep chiral concave around the metal center once coordinated to a transition metal. The two R groups on oxazoline rings of pybox form a highly enantioselective "chiral fence", which enables better differentiation of the Re and Si faces of incoming substrates. One property of the ligand ambox is a similar cyclic transition state as suggested by Noyori, and effectively catalyzation of asymmetric transformations-for instance, hydride-transfer reduction of ketones (FIG. 1). We disclosed the synthesis of bis[4-(R)-phenyloxazolin-2-yl-methyl)amine (1, (R)-ph-ambox) and its initial results from transfer hydrogenation of aromatic ketones before in Y. Jiang, Q. Jiang, X. Zhang, J. Am. Chem. Soc. 1998, 120, 3817. In the current invention, a direct asymmetric catalytic hydrogenation procedure using $H_2$ is presented using the Ru-ambox system. Compared with the transfer asymmetric hydrogenation system, the direct hydrogenation system offers many advantages: 1) the reaction is irreversible and 100% conversion can be achieved with high substrate concentration, 2) mild reaction condition such as about 5 atom $H_2$ pressure can be used and the reaction is clean; 3) the reaction is highly practical and scalable because >1000 turnovers can be conveniently achieved; 4) a large number of ketones and in-dries can be reduced with the current system for the efficient synthesis of alcohols and amines.

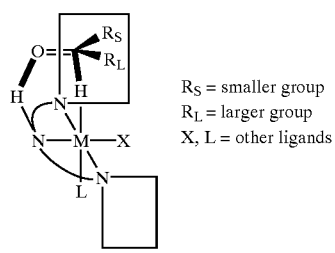

$R_S$ = smaller group
$R_L$ = larger group
X, L = other ligands

Figure 9:
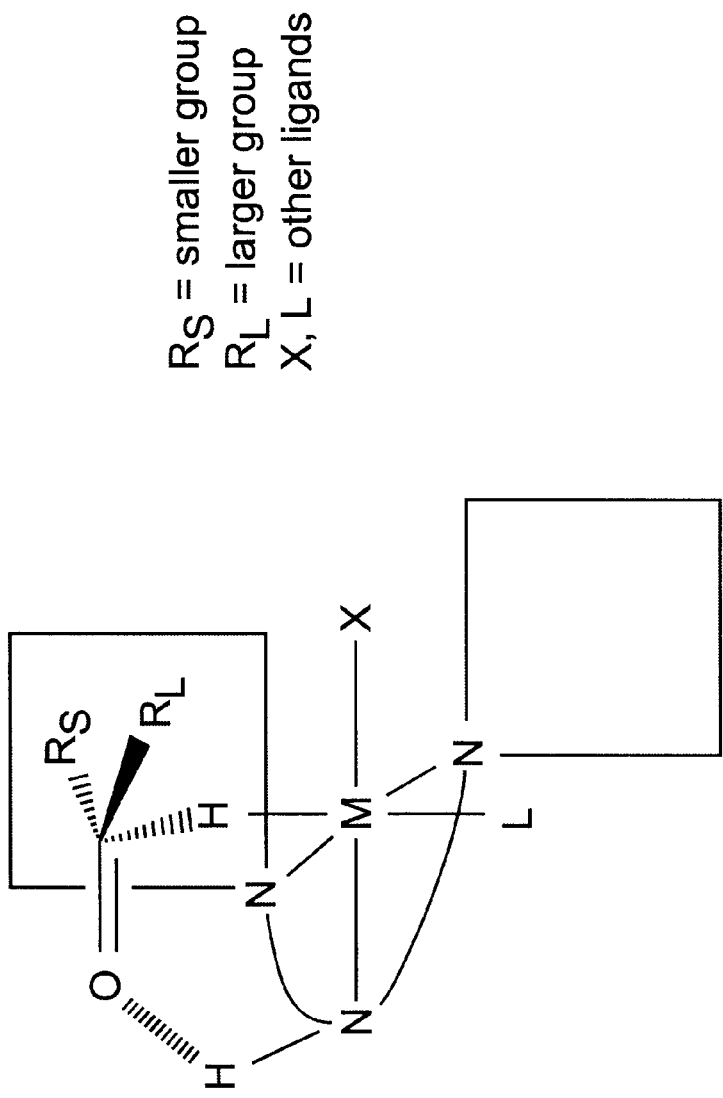
Figure 3:
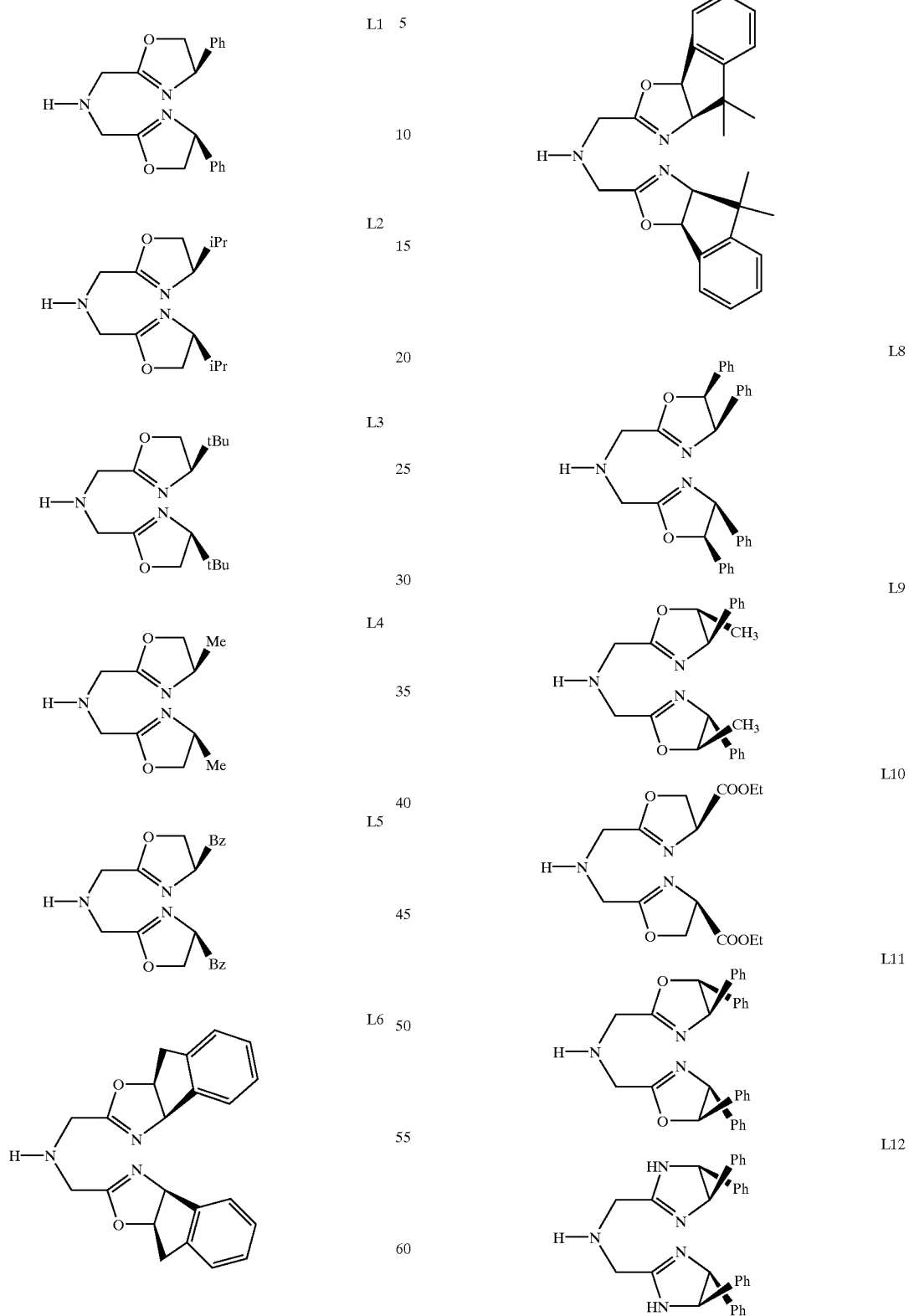
Figure 6:
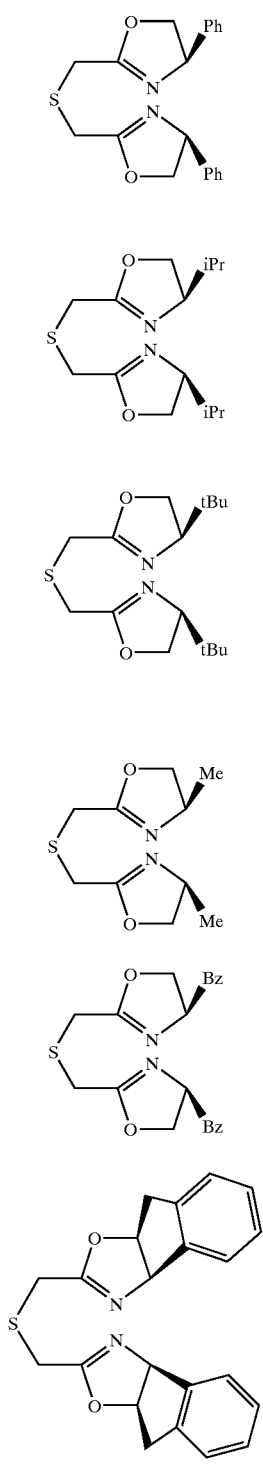
FIG. 6 shows examples of ligands (L37 to L48)
Figure 8:
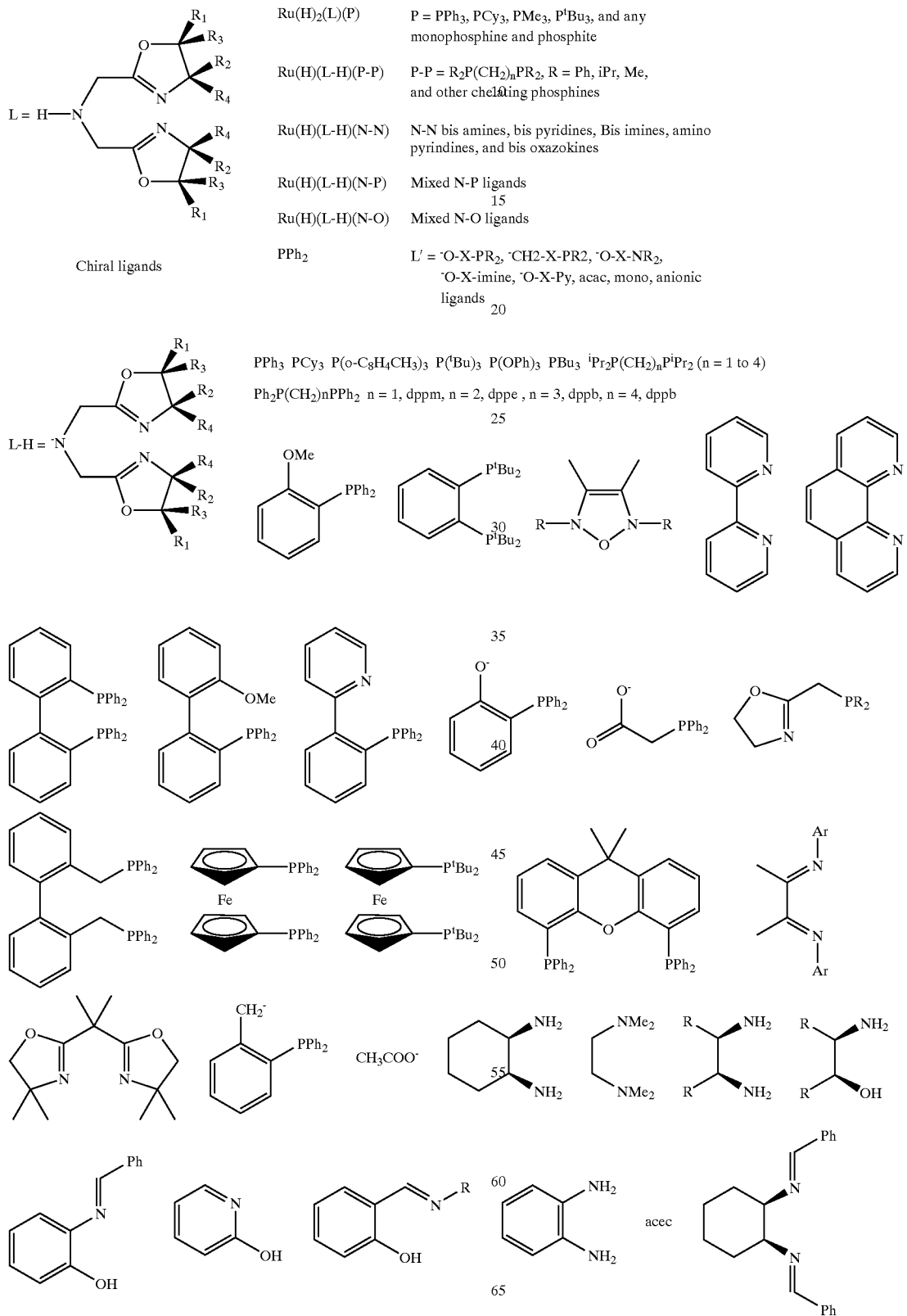

Schemetic depiction of transition metal catalysts of chiral tridentate nitrogen ligands with an NH function. Cycli (transition state of transfer hydrogenation of prochiral ketones (see FIG. 9).

Under the optimal conditions, a variety of aromatic ketones have been reduced to their secondary alcohols with high ee and mostly satisfactory yield (Table 1). Both ee and chemical yield are delicately affected by substrates' steric and electronic properties. The steric hindrance effect of the alkyl sides of ketone substrates is apparent.

TABLE 1

Enantioselective Hydrogenation of Aryl Ketones Catalyzed by (R)-Ph-Ambox-[RuCl$_2$(PPh$_3$)$_3$][a] System.

| entry | ketone | | $P_{H2}$ atm | t hr | conversion %[b] | ee %[b] |
|---|---|---|---|---|---|---|
| 1 | | X = CH$_3$ | 5 | 12 | 100 | 98 |
| 2 | | X = Et | 5 | 12 | 100 | 96 |
| 3 | | X = CH$_3$ | 5 | 12 | 100 | 99 |
| 4 | | C = Cl | 5 | 12 | 100 | 96 |
| 5 | | X = CH$_3$O | 5 | 12 | 14 | 81 |
| 6 | | | 30 | 12 | 24 | 88 |
| 7 | | X = CH$_3$ | 5 | 12 | 100 | 96 |
| 8 | | | 30 | 12 | 100 | 98 |
| 9 | | X = Cl | 5 | 12 | >99 | 84 |
| 10 | | | 30 | 12 | 100 | 81 |
| 11 | | X = CH$_3$O | 5 | 12 | 100 | 96 |
| 12 | | | 30 | 12 | 100 | 98 |
| 13 | | X = CH$_3$ | 5 | 12 | 100 | 98 |
| 14 | | X = Cl | 5 | 12 | 100 | 87 |
| 15 | | C = CH$_3$O | 5 | 12 | >99 | 95 |
| 16 | | | 30 | 12 | 100 | 93 |
| 17 | | | 5 | 24 | 87 | 94 |
| 18 | | | 30 | 12 | 80 | 81 |
| 19 | | | 5 | 24 | 97 | 90 |
| 20 | | | 30 | 12 | 88 | 80 |

TABLE 1-continued

Enantioselective Hydrogenation of Aryl Ketones
Catalyzed by (R)-Ph-Ambox-[RuCl₂(PPh₃)₃]ᵃ System.

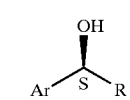

$$\underset{Ar}{\overset{O}{\|}}\!\!\!\!\!\!-\!\!\!\!R \;+\; H_2 \xrightarrow[\text{Pr}^i\text{OH, NaOPr}^i,\text{ rt}]{(R)-\text{Ph-Ambox-}[\text{RuCl}_2(\text{PPh}_3)_3]} \underset{Ar}{\overset{OH}{\underset{S}{\|}}}\!\!\!\!\!\!-\!\!\!\!R$$

| entry | ketone | $P_{H2}$ atm | t hr | conversion %[b] | ee %[b] |
|---|---|---|---|---|---|
| 21 | 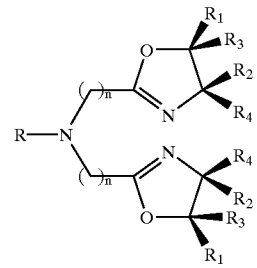 | 5 | 12 | 100 | 97 |
| 22 | 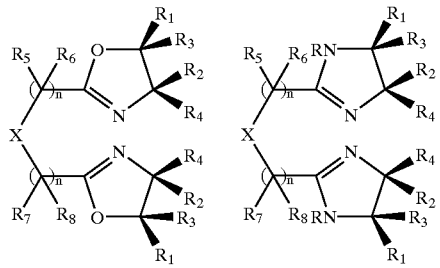 | 5 | 12 | >99 | 94 |
| 23 |  | 30 | 12 | 100 | 95 |

[a]See text for experimental procedures. The reactions were carried out at rt using a 0.2M ketone solution in 2 mL of 2-propanol. Ketone:Ru:1:NaOPr = 100:1:1.1:2.5.
[b]% ee and % conversion were determined by GC analysis with Supelco chiral capillary columns. Absolute configurations were determined by comparing optical rotations with literature values. All major secondary alcohol products are of the S configuration.

Catalytic Hydrogenation Procedures: In a flame-dried 50 mL Schlenk flask was added [RuCl₂(PPh₃)₃] (38 mg, 0.04 mmol) and 20 mL 2-propanol, followed by 0.44 mL (R)-Ph-Ambox ligand solution (0.1 M in toluene). The reaction was stirred under nitrogen on an oil bath (82° C.) for 5 hours, giving a clear dark green solution. After the removal of solvent on high vacuum, the greenish residue was washed with freshly distilled diethyl ether (3×5 mL). It was then redissolved in 20 mL 2-propanol and divided into ten equal parts. To each part (2 mL) of the catalyst solution was introduced 0.4 mmol of a ketone substrate. The reaction mixture was stirred at rt for a brief period before 0.1 mL of NaOPr$^i$ solution (0.1 M in 2-propanol) was finally added in one portion. The ten reaction ampuls were placed in an autoclave and charged with hydrogen gas (initial pressure 5 atm). The reactions were allowed to stir at rt overnight.

A small portion of each reaction mixture was passed through a silica gel plug, then eluted with diethyl ether. Both reaction conversion and enantiomeric excess were then determined by GC analysis.

References
1. Reviews: (a) Zassinovich, G.; Mestroni, G.; Gladiali, S. *Chem. Rev.* 1992, 92, 1051. (b) de Graauw, C. F.; Peters, J. A.; van Bekkum, H.; Huskens, J. *Synthesis* 1994, 1007.
2. (a) Jiang, Y.; Jiang, Q.; Zhu, G.; Zhang, X. *Tetrahedron Lett.* 1997, 38, 215. (b) Jiang, Y.; Jiang, Q.; Zhu, G.; Zhang, X. *Tetrahedron Lett.* 1997, 38, 6565. (c) Jiang, Q. Z.; Van Plew, D.; Murtuza, S.; Zhang, X. *Tetrahedron Lett.* 1996, 37, 797. (d) Sammakia, T.; Stangeland, E. L. *J. Org. Chem.* 1997, 62, 6104. (e) Evans, D. A.; Nelson, S. G.; Gagné, M. R.; Muci, A. R. *J. Am. Chem. Soc.* 1993, 115, 9800. (f Muller, D.; Umbricht, G.; Weber, B.; Pfaltz, A. *Helv. Chim. Acta* 1991, 74, 232. (g) Langer, T.; Heimchen, G. *Tetrahedron Lett.* 1996, 37, 1381.
3. (a) Noyori, R.; Hashiguchi, S. *Acc. Chem. Res.* 1997, 30, 97. (b) Haack, K. J.; Hashiguci, S.; Fujii, A.; Ikariya, T.; Noyori, R. *Angew. Chem., Int. Ed. Engl.* 1997, 36, 285.
4. Gao, J.; Ikariya, T.; Noyori, R. *Organometallics* 1996, 15, 1087.
5. Gamez, P.; Fache, F.; Lemaire, M. *Tetrahedron: Asymmetry* 1995, 6, 705

FIG. 1

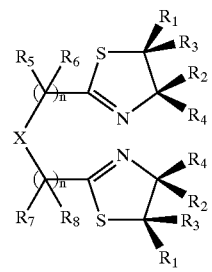

R, R1, R2, R3, R4 = H, alkyl, aryl, sunstituted alkyl, substituted aryl. Ring structure is also possible by linking any two R groups from R1 to R4. The ligands can be linked to solid supports.

FIG. 2

R, R1, R2, R3, R4, R5, R6, R7, R8 = H, alkyl, aryl, substituted alkyl, substituted aryl. Ring structure is also possible by linking any two R groups from R1 to R4. The ring can be alkyl, substituted alkyl, aryl, and substituted alryl. X = PR', PH, O, S, Se, AsR', AsH, SiR'H, GeR'H, NH, NR', NR'₂, NCOR', NOH, NNHR', NNHCOR' wherein R' = alkyl, aryl, substituted alkyl, and substituted aryl. n = 1, 2.

Figure 3:
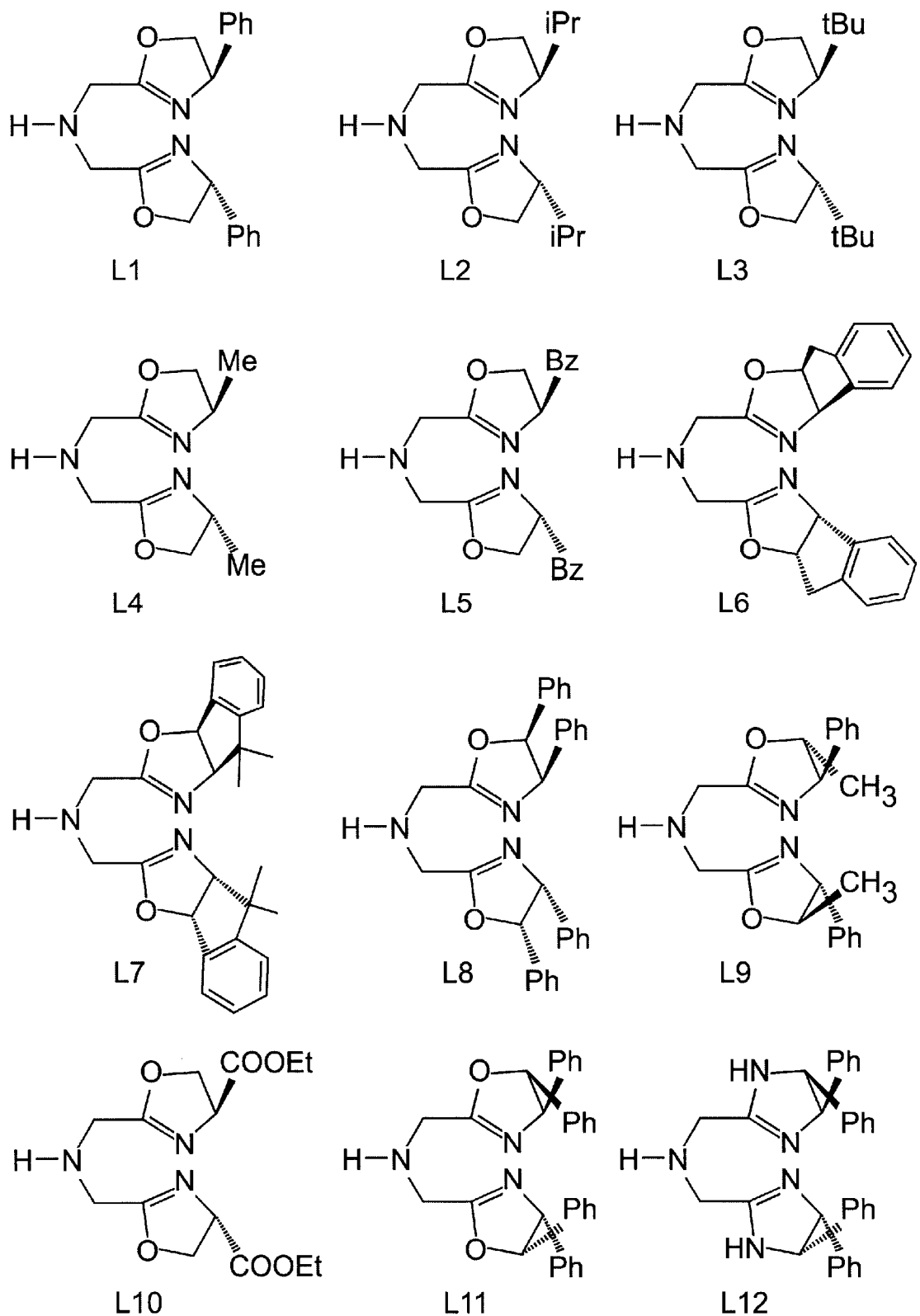
FIG. 3 shows examples of ligands (L1 to L12)
Figure 4:
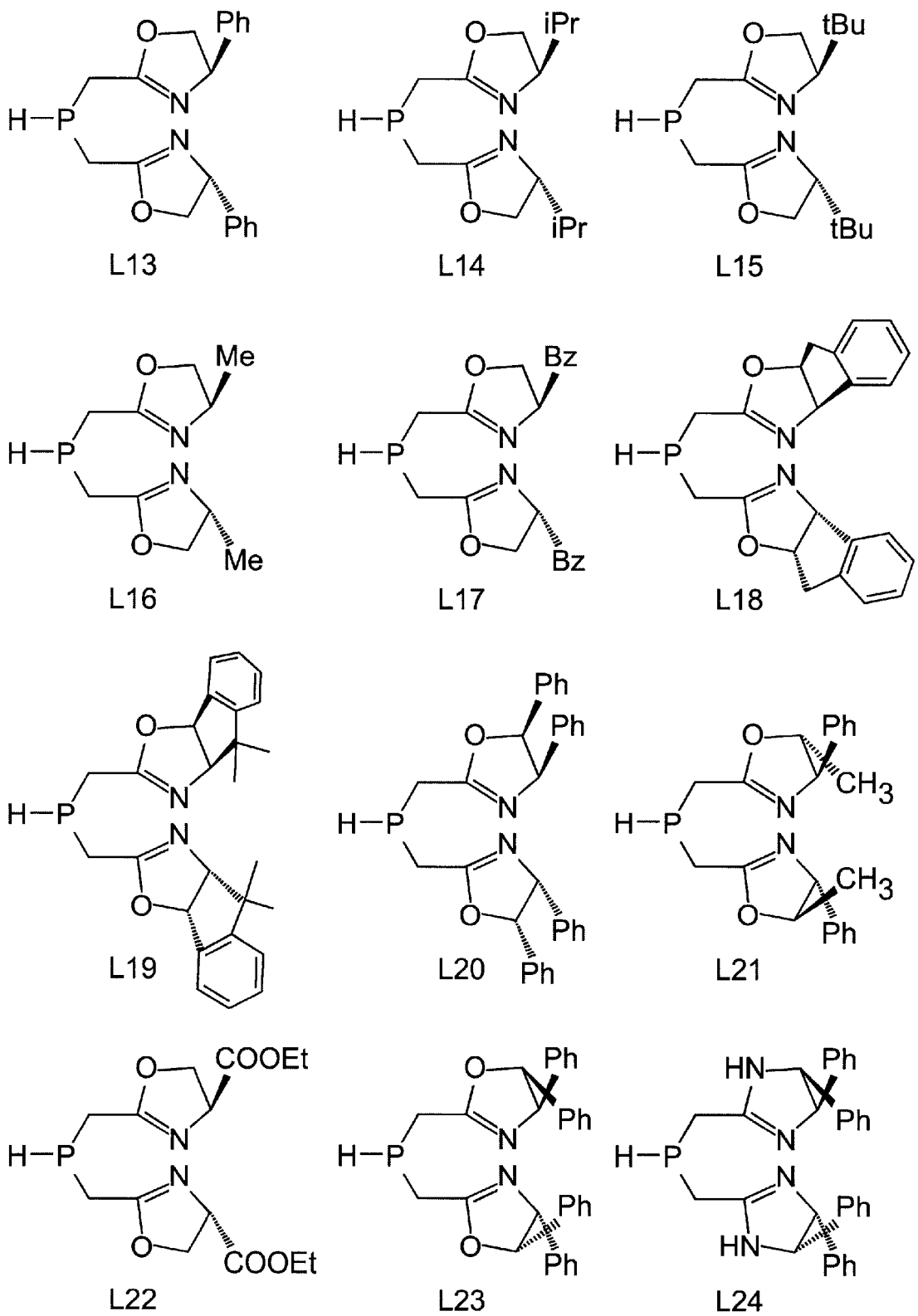
FIG. 4 shows examples of ligands (L13 to L24)

FIG. 4
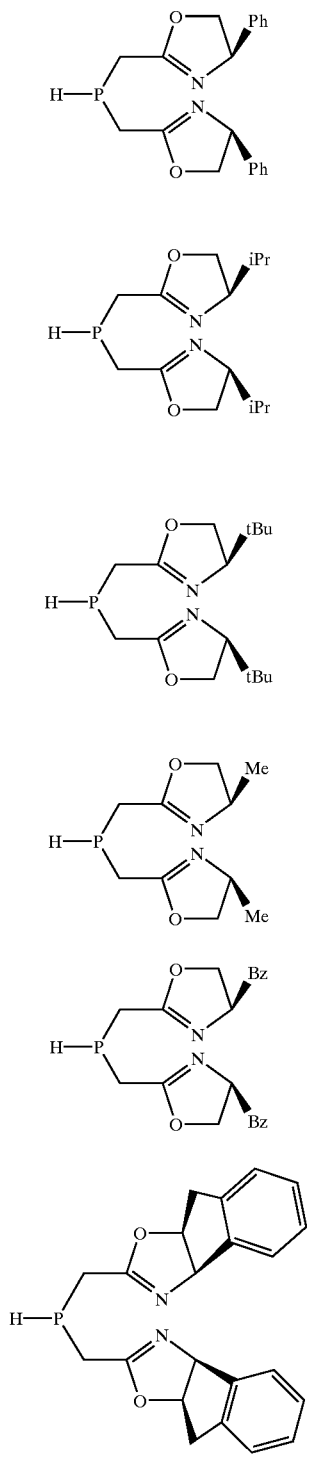
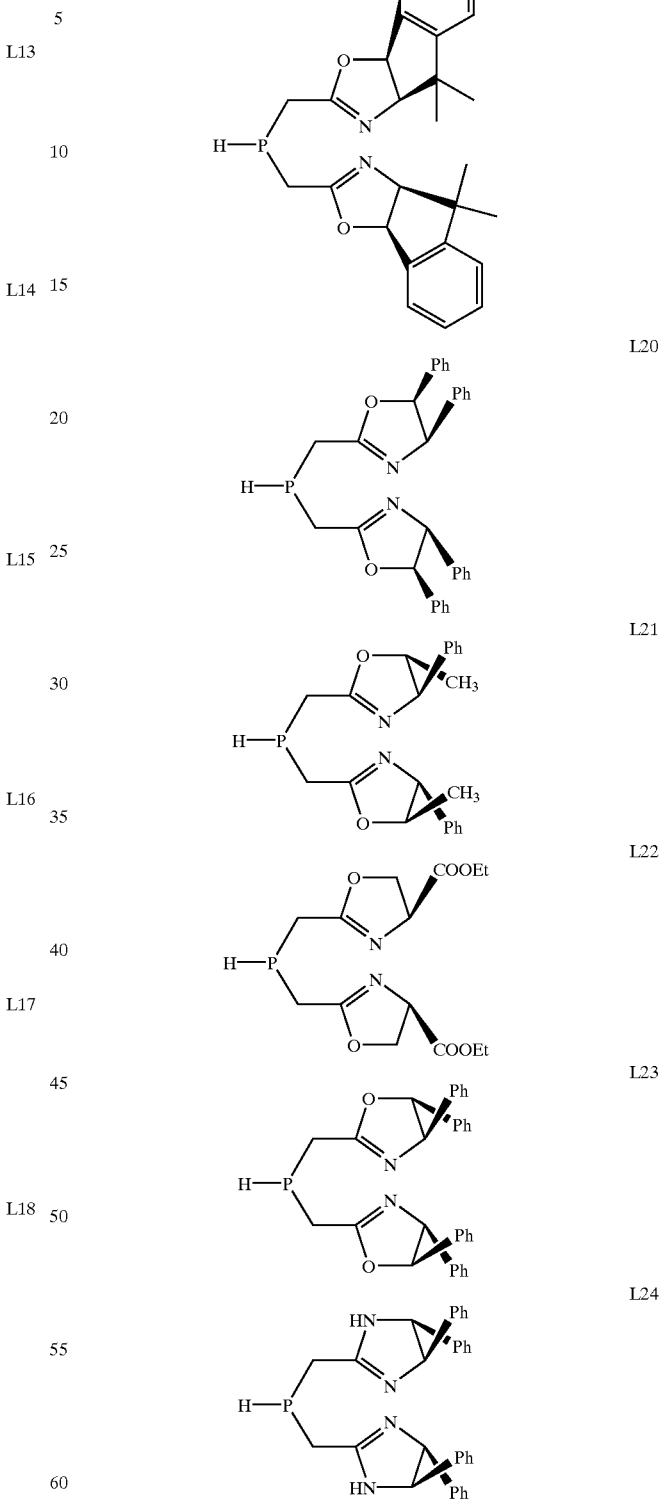

Figure 5:
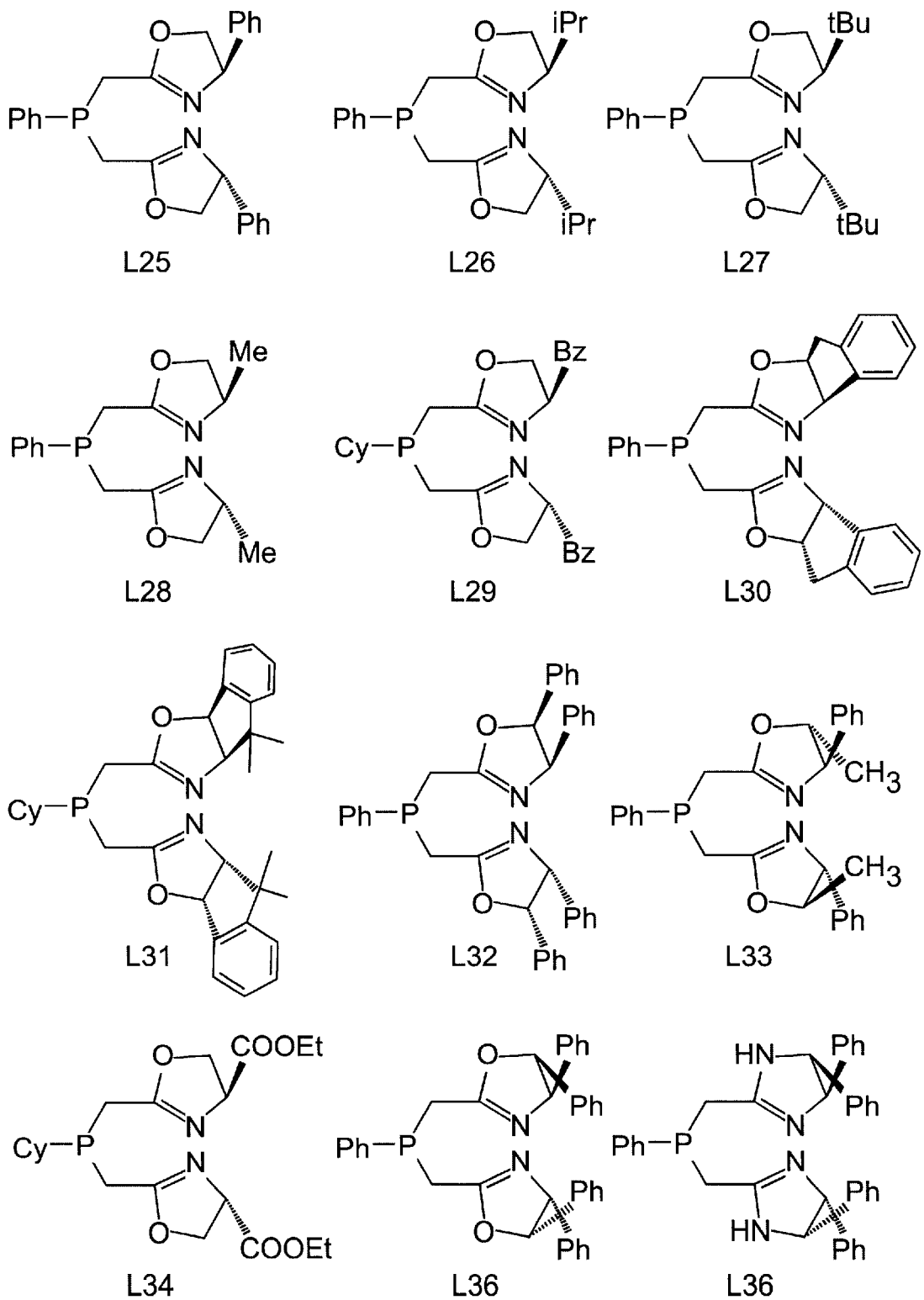
FIG. 5 shows examples of ligands (L25 to L36)
Figure 8:
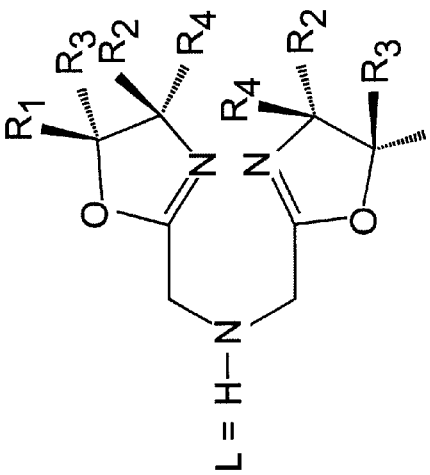
FIG. 8 shows Ru catalytic systems with a variety of modify ligands
Figure 8:
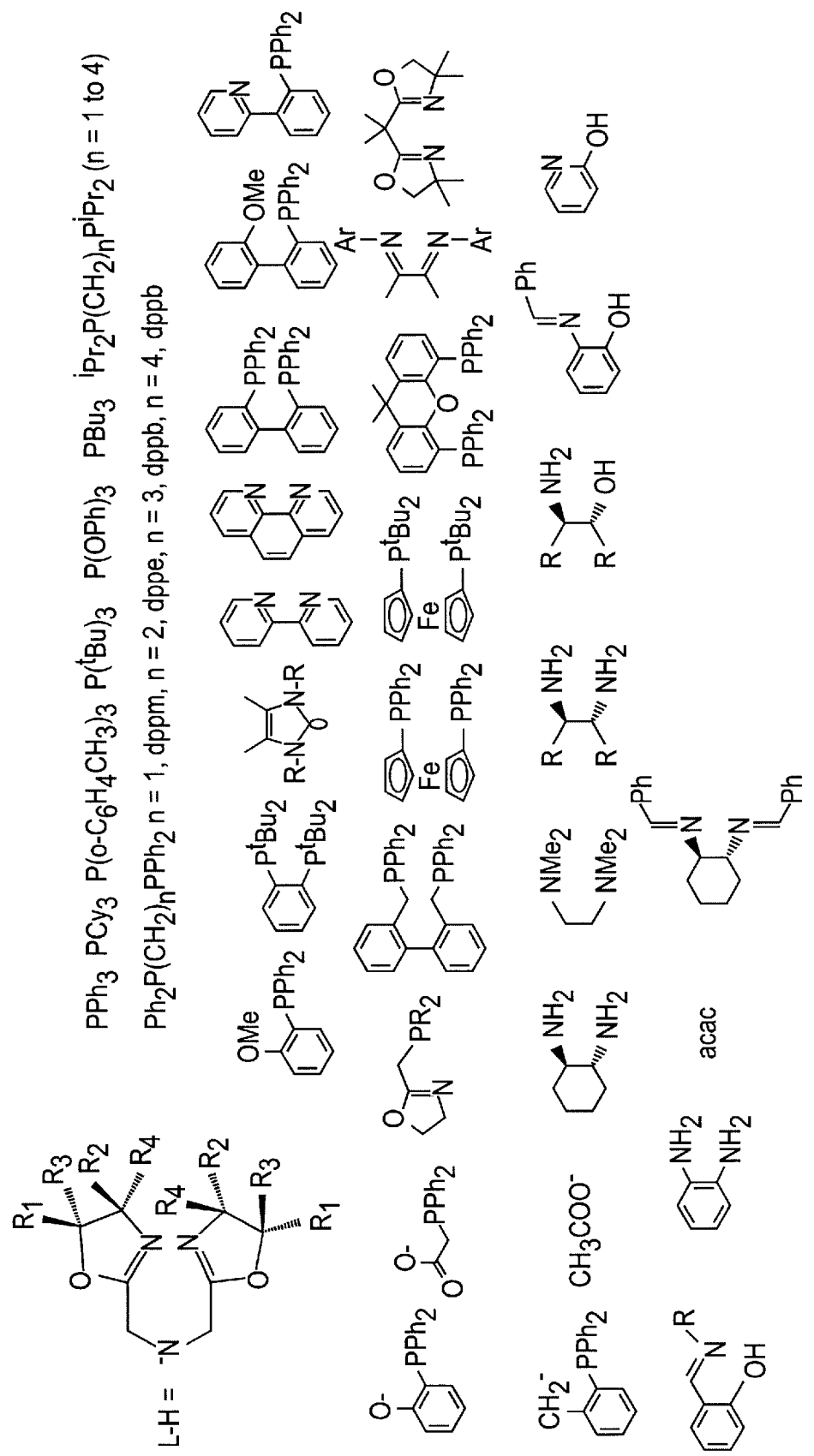

FIG. 5
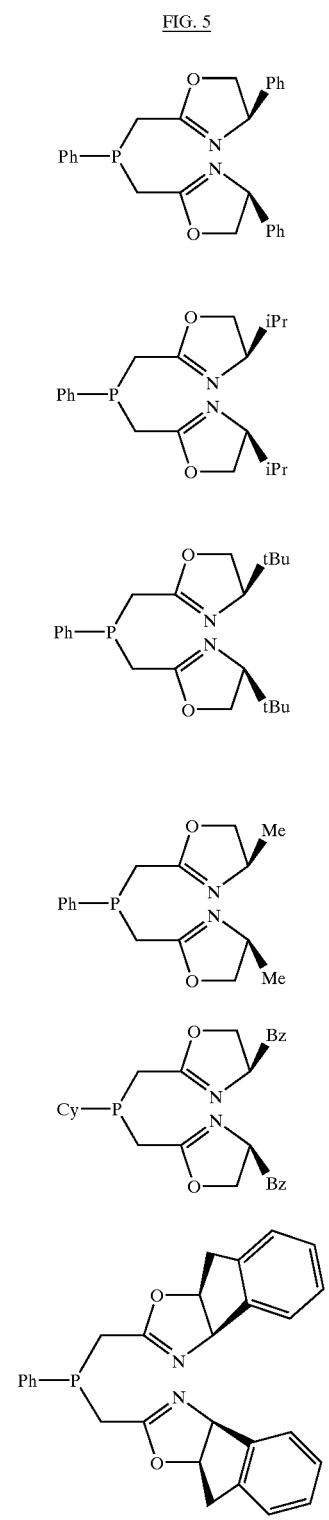
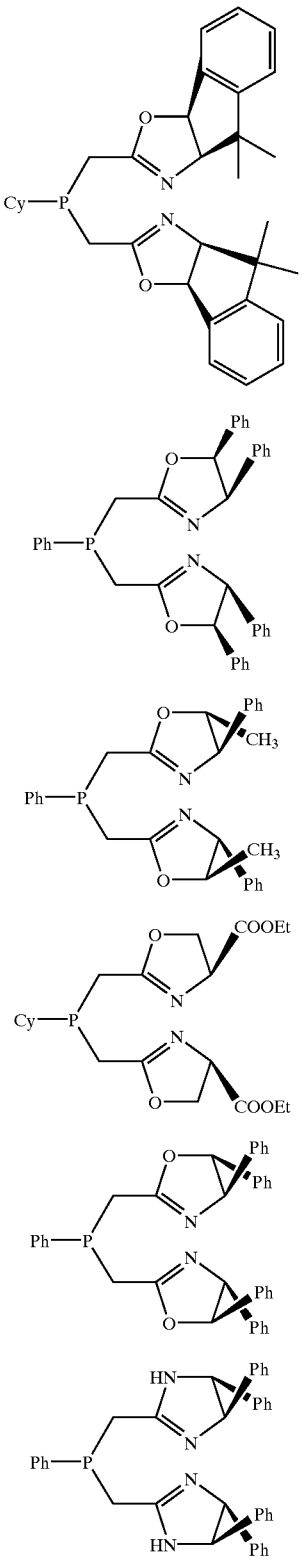

FIG. 7
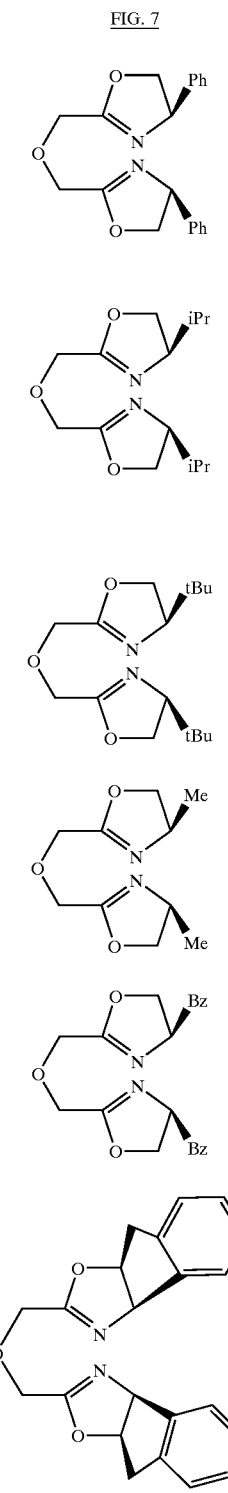
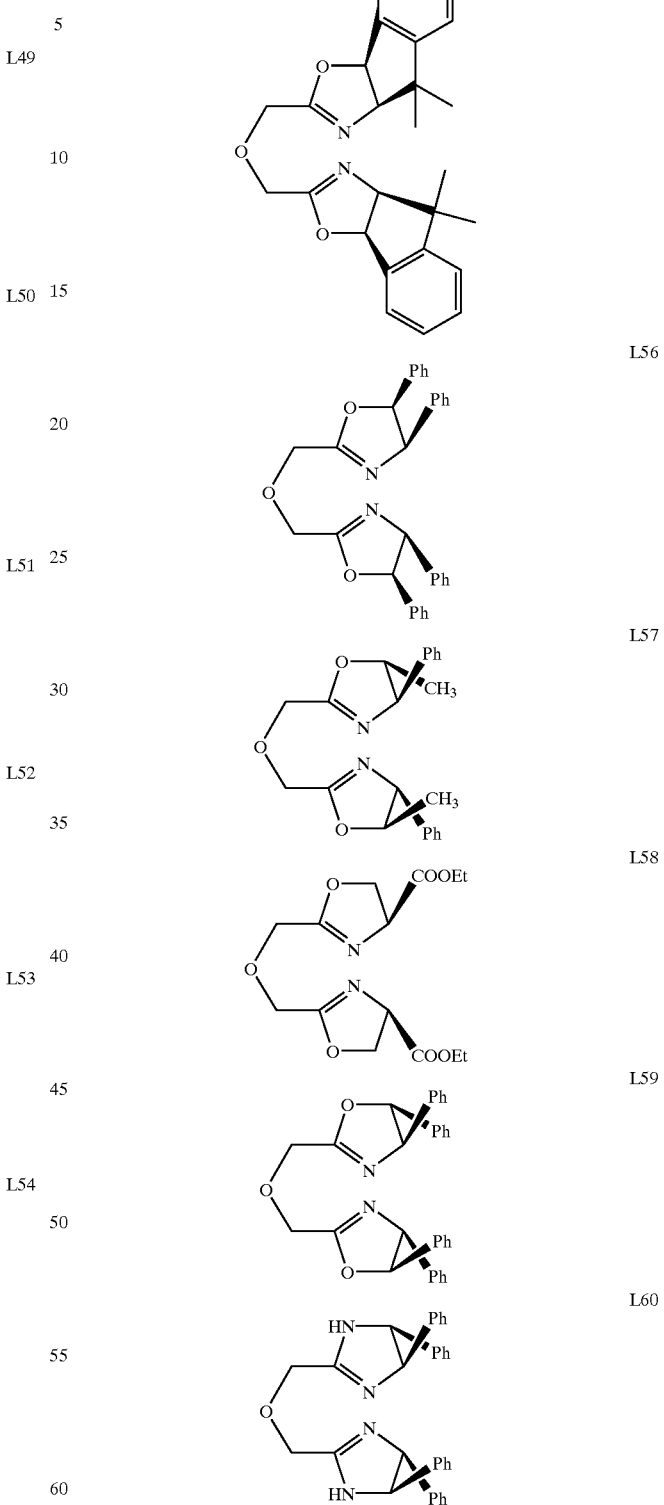

Catalysts for hydrogenation

FIG. 9

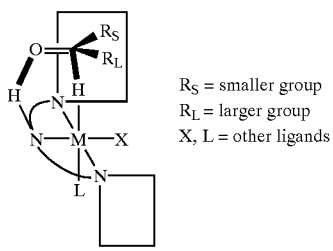

$R_S$ = smaller group
$R_L$ = larger group
X, L = other ligands

Schematic depiction of transition metal catalysts of chiral tridentate nitrogen ligands with an NH function. Cyclic transition state of transfer hydrogenation of prochiral ketones.

Scheme 1
Synthesis of Ligands

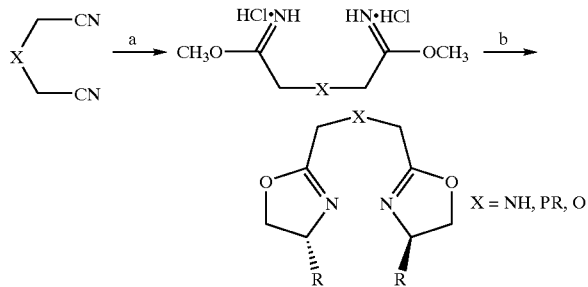

a. HCl, CH$_3$OH
b. amino alcohol, CH$_2$Cl$_2$, 0° C. to rt

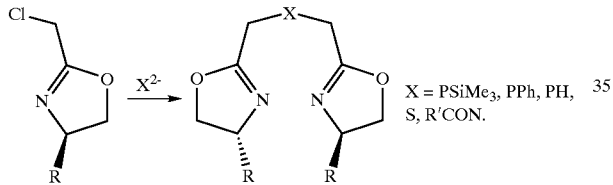

What is claimed is:

1. A compound selected from the enantiomer of formula (I), (II), and (III):

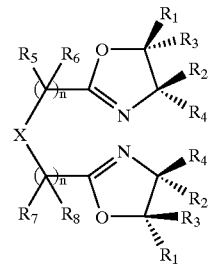

(I)

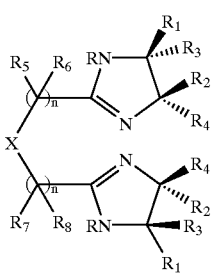

(II)

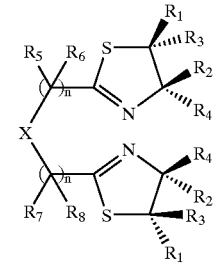

(III)

in which R, $R_1$, $R_2$, $R_3$, $R_4$, $R_5$, $R_6$, $R_7$ and $R_8$, are each independently selected to be the same or different and are selected from a hydrogen atom, an alkyl radical, an aryl radical, a substituted alkyl radical, and substituted aryl radical;

wherein any two of $R_1$, $R_2$, $R_3$, and $R_4$ when linked together form a ring; X is chosen from PR', PH, O, S, Se, AsR', AsH, SiR'H, GeR'H, NH, NR', NR'$_2$, NCOR', NOH, NNHR', and NNHCOR', wherein R' is selected from an alkyl radical, an aryl radical, a substituted alkyl radical, and a substituted aryl radical; and n is 1 or 2.

2. A compound according to claim 1, wherein said compound is selected from formulas (IV), (V), (VI), (VII), (VIII), and (IX):

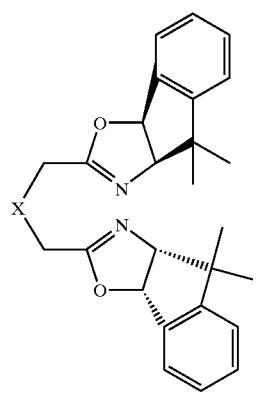

(IV)

(V)

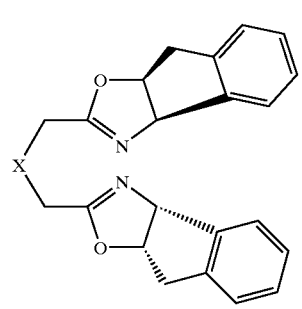

(VI)

-continued

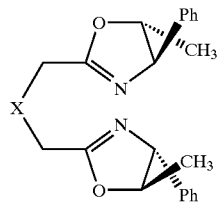
(VII)

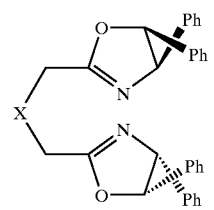
(VIII)

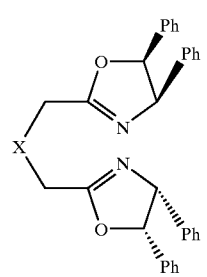
(IX)

wherein R₂ is selected from a phenyl radical, a methyl radical, an isopropyl radical, a tert-butyl radical, a benzyl radical and an ethoxycarbonyl group, and X is selected from NH, PH, S, and O.

3. A compound according to claim 1, wherein said compound is selected from formula (X):

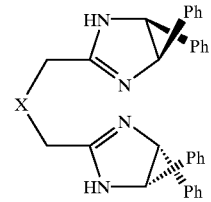
(X)

wherein X is selected from NH, S, PH, PPh and O.

4. A compound according to claim 1, wherein said compound is selected from formulas (XI), (XII), (XIII), (XIV), (XV), (XVI), (XVII), and (XVIII):

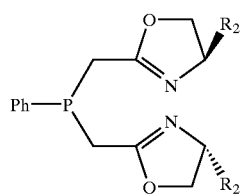
(XI)

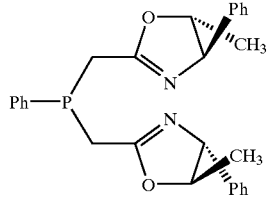
(XII)

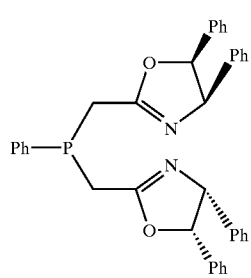
(XIII)

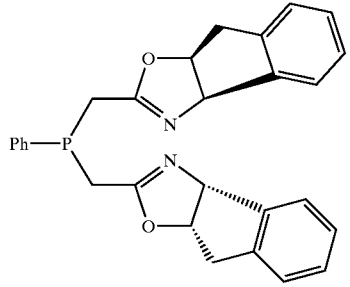
(XIV)

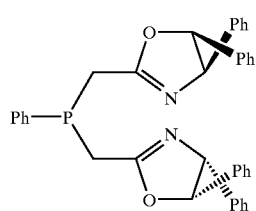
(XV)

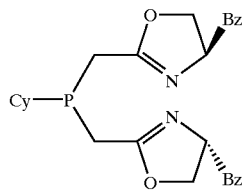
(XVI)

-continued (XVII)
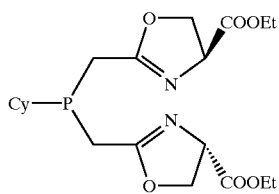

(XVIII)
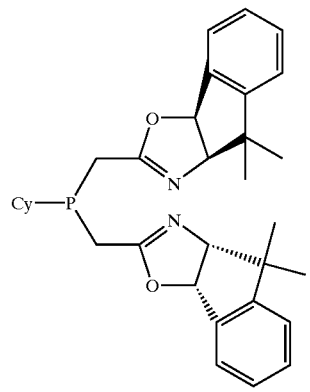

wherein R₂ is selected from a phenyl radical, an isopropyl radical, a tert-butyl radical, and a methyl radical.

5. A compound according to claim 1, wherein said compound is complexed with a transition metal.

6. A compound according to claim 5, wherein said transition metal is selected from rhodium, iridium, ruthenium, platinum and palladium.

7. A Process for making a compound of claim 1 comprising reacting an imidate ester with a chiral alcohol to form a chiral ligand.

8. A process according to claim 7, further comprising complexing said chiral ligand with a transition metal catalyst compound wherein said transition metal catalyst precursor comprises a transition metal.

9. A process according to claim 8, wherein said transition metal catalyst precursor is triphenylphosphine, and wherein said process further comprises removing free triphenylphosphine released during complexation of said chiral ligand with said transition metal catalyst precursor.

10. A process according to claim 8, further comprising refluxing said catalyst precursor and said chiral ligand with an alcohol at the reflux temperature of the alcohol.

11. A process according to claim 8, wherein said transition metal is at least one transition metal selected from rhodium, iridium, ruthenium, and palladium.

12. A process according to claim 7, wherein said catalyst precursor is selected from [Rh(cod)Cl]₂, [Rh(cod)₂]Y, [Ir(cod)Cl]₂, and [Ir(cod)₂]Y, wherein cod is 1,5-cyclooctadiene, and Y is $BF_4$, $ClO_4$, $SbF_6$, or $CF_3SO_3$.

13. A process according to claim 7, wherein said catalyst precursor is selected from RuCl₂(PPh₃)₃, RuHCl(PPh₃)₃, RuZ₂(PR₃)₃, RuHZ(PR₃)₃ and RuZ₂, wherein Z is halogen and R is a substituted or unsubstituted alkyl or aryl group.

* * * * *

UNITED STATES PATENT AND TRADEMARK OFFICE
CERTIFICATE OF CORRECTION

PATENT NO. : 6,476,233 B1
DATED : November 5, 2002
INVENTOR(S) : Xumu Zhang

It is certified that error appears in the above-identified patent and that said Letters Patent is hereby corrected as shown below:

Column 1,
Line 13, insert the following:
-- GOVERNMENT SPONSORSHIP
 This invention was made with support from the Government under Contract No. N00014-96-1-0733 and the National Institutes of Health under NIH Grant No. 1R01 GM58832. The Government has certain rights in the invention. --

Signed and Sealed this

Third Day of May, 2005

JON W. DUDAS
*Director of the United States Patent and Trademark Office*